(12) United States Patent
Campuzano

(10) Patent No.: US 6,786,074 B1
(45) Date of Patent: Sep. 7, 2004

(54) SHOCK ABSORBER DYNAMOMETER

(76) Inventor: Pedro Campuzano, 533 Skokie Ave., Highland Park, IL (US) 60035

( * ) Notice: Subject to any disclaimer, the term of this patent is extended or adjusted under 35 U.S.C. 154(b) by 0 days.

(21) Appl. No.: 10/407,299

(22) Filed: Apr. 4, 2003

Related U.S. Application Data

(60) Provisional application No. 60/370,471, filed on Apr. 5, 2002.

(51) Int. Cl.[7] .................................................. G01N 3/30
(52) U.S. Cl. ........................................................ 73/11.04
(58) Field of Search .............................. 73/11.04–12.14, 73/865.8, 865.9

(56) References Cited

U.S. PATENT DOCUMENTS 3,498,115 A * 3/1970 Liskey ......................... 73/654
3,913,388 A * 10/1975 Berner et al. ................. 73/634
4,426,683 A * 1/1984 Kissell ....................... 73/12.07
5,396,973 A * 3/1995 Schwemmer et al. ..... 188/267.1
5,923,487 A * 7/1999 Carlson et al. ............... 360/60

* cited by examiner

Primary Examiner—Edward Lefkowitz
Assistant Examiner—Takisha Miller
(74) Attorney, Agent, or Firm—Brinks Hofer Gilson & Lione

(57) ABSTRACT

A shock dynameter provides for testing, measurement, and quantification of suspension shock absorbers, also known as suspension dampers, particularly as fitted to small and scale vehicles. The shock dynamometer provides a reliable, convenient, economical, and compact method and device for testing suspension shock absorbers.

20 Claims, 5 Drawing Sheets

SHOCK ABSORBER DYNAMOMETER

The present application claims the benefit of U.S. Provisional Application No. 60/370,471, filed Apr. 5, 2002, titled Shock Absorber Dynamometer.

FIELD OF THE INVENTION

The present invention relates to a device for the testing and quantifying of suspension shock absorbers, specifically as fitted to the suspension systems of vehicles. In particular, the present invention is related to a shock absorber dynamometer.

BACKGROUND OF THE INVENTION

In the past, shock absorber dynamometers took the form of electrically, pneumatically or hydraulically driven apparatus. In operation, the dynamometers tested a fitted suspension shock absorber by actuating the fitted shock absorber with a complex electrical, pneumatic, or hydraulic drive system. The dynamometers often provided numerical or graphical data for comparison and relation of modifications and adjustments to the dampening characteristics of the fitted shock absorber to modified versions of itself and to other shock absorbers. However, shock absorber dynamometers were large and complex because they were used to test large or full-scale suspension shock absorbers as fitted to large or full-scale vehicles.

Part of the complexity in past dynamometers arose, in part, due to their drive systems. In particular, the drive systems required external power sources and complex control systems to maintain reliable speed and/or force of actuation. Thus, prior dynamometers were comparatively large due to the requirements of these drive systems and relatively expensive due to the components necessary for accurate and reliable actuation and measurement.

SUMMARY OF THE INVENTION

The present shock dynamometer provides a convenient, reliable, compact and relatively inexpensive device to test and quantify small and scale suspension shock absorbers as used on small and scale vehicles.

The dynamometer includes a drive system that is actuated by the energy of a falling weight of predetermined mass. This weight is attached to a cable of predetermined length wound around a spool of predetermined diameter that rotates a shaft onto which a crank is fixed. The shock absorber is fitted to the crank and the upper end of the shock absorber is fixed to a tower. When the weight is released, the crank actuates the shock absorber through a predetermined number of rotations or cycles. One rotation or cycle of the crank comprises one compression stroke and one extension stroke of the fitted shock absorber. A trigger mounted to the drive shaft of the unit allows a timing device to compute and display the dampening effect of the fitted shock absorber upon the fall of the weight.

A drive comprising a falling weight is convenient and reliable because no external power sources or complex control systems are required. Furthermore, the reliability and consistency of the drive speed and force are only effected by the small fluctuations in the force of Earth's gravity. The reduced complexity of the drive system and of the timing and display unit allow the dynamometer to be manufactured relatively inexpensively and easily sized for its intended use.

DETAILED DESCRIPTION

As an initial matter, it is noted that the shock absorbers to be tested by the following described embodiment of a shock dynamometer are those shock absorbers generally fitted to radio-controlled (also known as remote-controlled) vehicles of scales of 1/18 to 1/4 of a full size vehicle. The shock absorbers tested by the dynamometer are, for example, fluid or friction dampened shock absorbers ranging in size from 1.150" to 3.600" from the center of the top mount to center of the bottom mount with the shock absorber at full compression. In one implementation of the dynamometer, the minimum stroke of the shock absorber to full extension is 0.200" and the average body diameter of the shock absorbers to be tested is 0.500".

Figure 1:
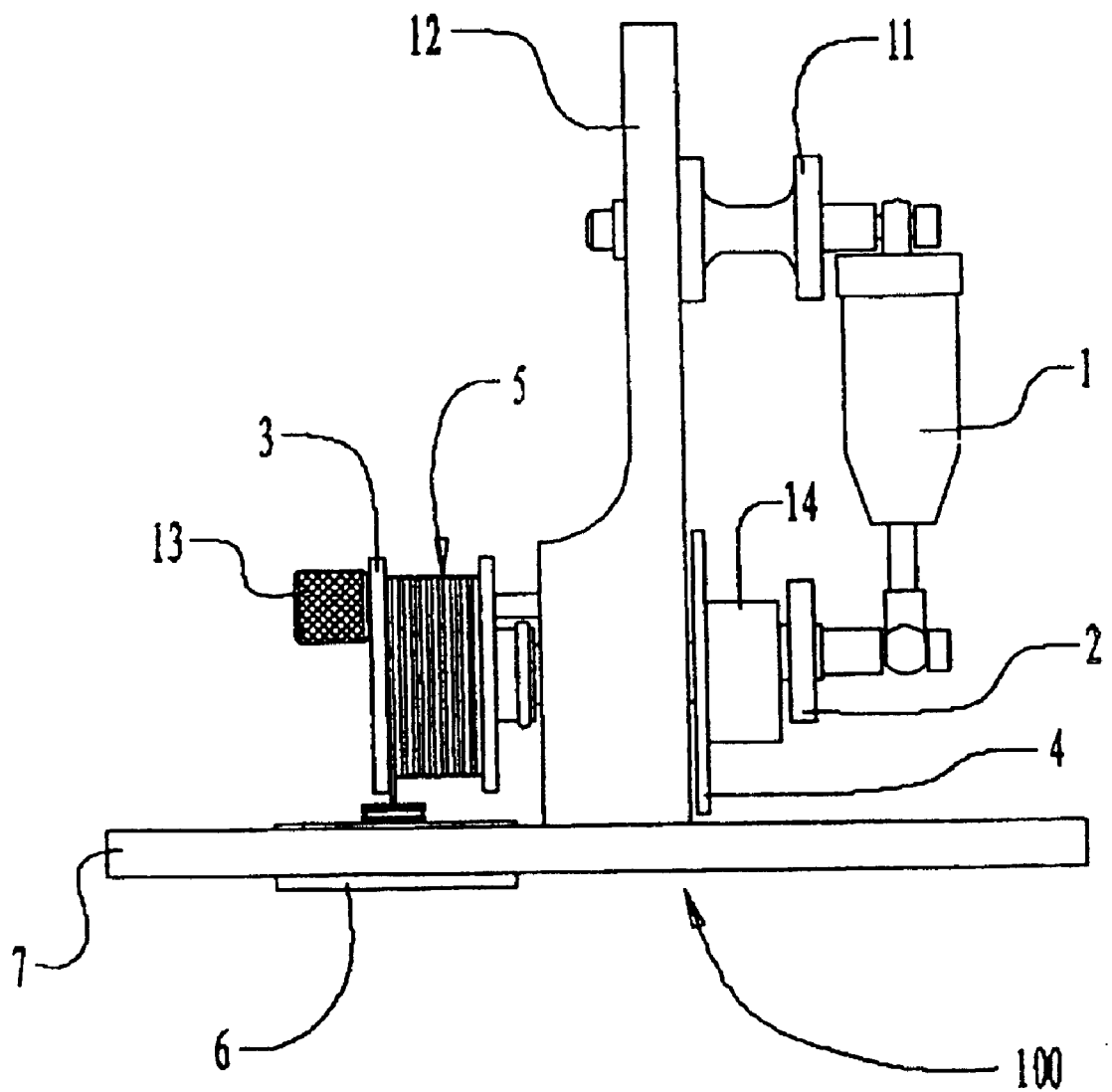
FIG. 1 is a side view of one embodiment of a shock dynamometer.
Figure 2:
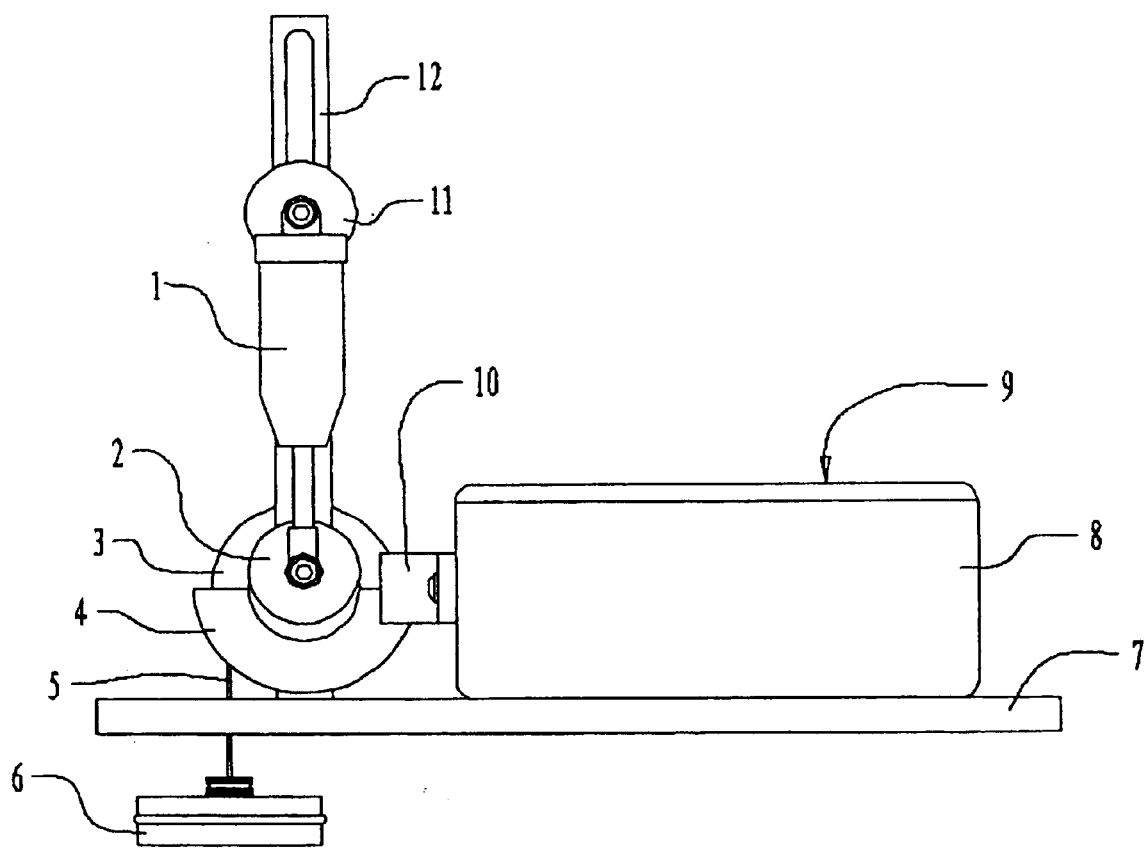
FIG. 2 is a front view of the embodiment shown in FIG. 1.

Referring now to FIGS. 1 and 2, a shock dynamometer 100 is shown that includes a shock dynamometer base 7. The base 7 may be implemented as a machined 6061-T6 aluminum alloy plate of sufficient thickness and size to ensure secure mounting of the shock dynamometer components and a stable platform of operation. For example, the plate may be 7.00" by 3.50" by 0.250". The tower 12 is of machined 6061-T6 aluminum alloy and may be, for example, 4.80" by 0.750" by 0.500". The tower 12 supports the test shock absorber 1 at its upper mount using a mount bobbin 11. The tower 12 also supports the drive system components, parts 2, 3, 4, 5, 6, 13 and 14.

The tower 12, as dimensioned above, is of sufficient height to carry the intended range of shock absorbers to be tested. The tower 12 is vertically slotted 2.50" to allow adjustability in this range using mount bobbin 11. The mount bobbin 11 is machined of aluminum alloy and unequally threaded at the mount and clamp ends to allow the fitment of the intended range of shock absorbers. The mounting of the shock absorbers to be tested may adhere to the ANSI and/or ANSI-M standards, or a combination thereof. The mount for this embodiment is thus tapped 4–40 UNC at one end and 3 mm–0.5 at the other. For an ANSI mounted shock, the 3 mm–0.5 end is inserted and clamped to the tower and the shock is mounted to the 4–40 UNC end. By turning the bobbin around, inserting and clamping the 4–40 end in the tower, a shock designed for ANSI-M mounting may be tested by the dynamometer 100.

The lower mounting of the shock absorber is fastened to the rotator mount 2, which is machined of aluminum alloy and unequally threaded as the mount bobbin 11 to allow for flexibility in fitting as described above. The shock absorber 1 is mounted to one end of the rotator mount 2, with the opposing end of the rotator mount 2 inserted into the drive crank 14, as shown in FIG. 1. The rotator mount 2 is offset from the centerline of the drive crank main shaft by 0.100". As the crank rotates, the shock absorber to be tested is thus actuated or stroked 0.200". The rotator mount 2 is carried in the drive crank 14 by two 0.375"O.D.x0.250"I.D.x0.125" bearings to minimize the rotational drag of the lower shock mount so that it does not significantly effect the overall dampening of the shock absorber upon the shock dynamometer drive system.

The above mentioned drive crank main shaft 14 is machined of 6061-T6 aluminum alloy. The drive crank main shaft rides on two 0.375"O.D.×0.250"I.D.×0.125" bearings pressed into tower 12. The drive cable spool 3 is slid over and pinned to the drive shaft. The drive cable spool 3 is machined of aluminum alloy and sized to carry the desired gauge and turns of the drive cable 5. The gauge and length of the drive cable 5, which is nylon covered multistrand steel cable or a suitable alternative, is dependent on the range of shock absorbers to be tested and the mass of drive weight 6, which is attached to the drive cable. For this embodiment the drive spool is 1.00" diameter with 29.50" of 0.035" nylon coated stainless cable.

The drive weight 6 is machined in brass and of sufficient mass to actuate the intended range of shock absorbers to be tested. In one embodiment, the mass may be 75 grams. The drive system is locked from rotation when not in use by lock pin 13, which is fabricated of 0.125" steel rod with a pressed-on aluminum alloy knob. The lock pin passes through the drive spool 3 and pins into the tower 12. When released the drive weight falls and rotates the shaft by the unwinding of the drive cable from the spool. As a result, the shock absorber is actuated through the drive crank and rotator mount.

The trigger plate 4 is a stamped semicircle of 0.060" aluminum alloy plate with a radius of 0.750" mounted to the drive crank as shown in FIG. 2. The trigger plate 4 passes through the optical interrupter switch 10. For this embodiment, an Omron Electronics EE-SG3 is used as the optical interrupter switch 10. The optical interrupter switch; is mounted to the side of the timing and data display box 8 shown in FIG. 2. As the shock is actuated, the trigger plate rotates through the optical interrupter switch. The trigger plate is fastened to the drive crank in such a manner that as the crank is compressing the shock absorber; that is, moving the shaft of the shock absorber into the body of the shock absorber; the trigger plate is passing through the optical switch 10 creating an open circuit.

As the drive crank extends the shock absorber, or pulls the shaft of the shock absorber out of the shock body, the optical switch 10 does not detect the trigger plate thus creating a closed circuit. One rotation of the drive crank is one compression and one extension of the shock absorber. For one half of the rotation the optical switch 10 is an open circuit (during shock compression) and for the other half of rotation the optical switch 10 is a closed circuit (during shock extension).

The drive system actuates the shock absorber 1 through a number of rotations determined by the length of the drive cable, for this embodiment eight and one half turns. The number of turns may be varied, however, to be greater or fewer, depending on the particular implementation. As described in more detail below, using a microprocessor, the timing and data display controller 8 records for each rotation the time that the optical switch 10 is an open circuit and the time that the optical switch 10 is a closed circuit for a preselected number of rotations. The preselected number of rotations may be, for example, one less rotation than that of the drive system total number of rotations (in this embodiment the dynamometer 100 measures seven rotations).

Figure 3:
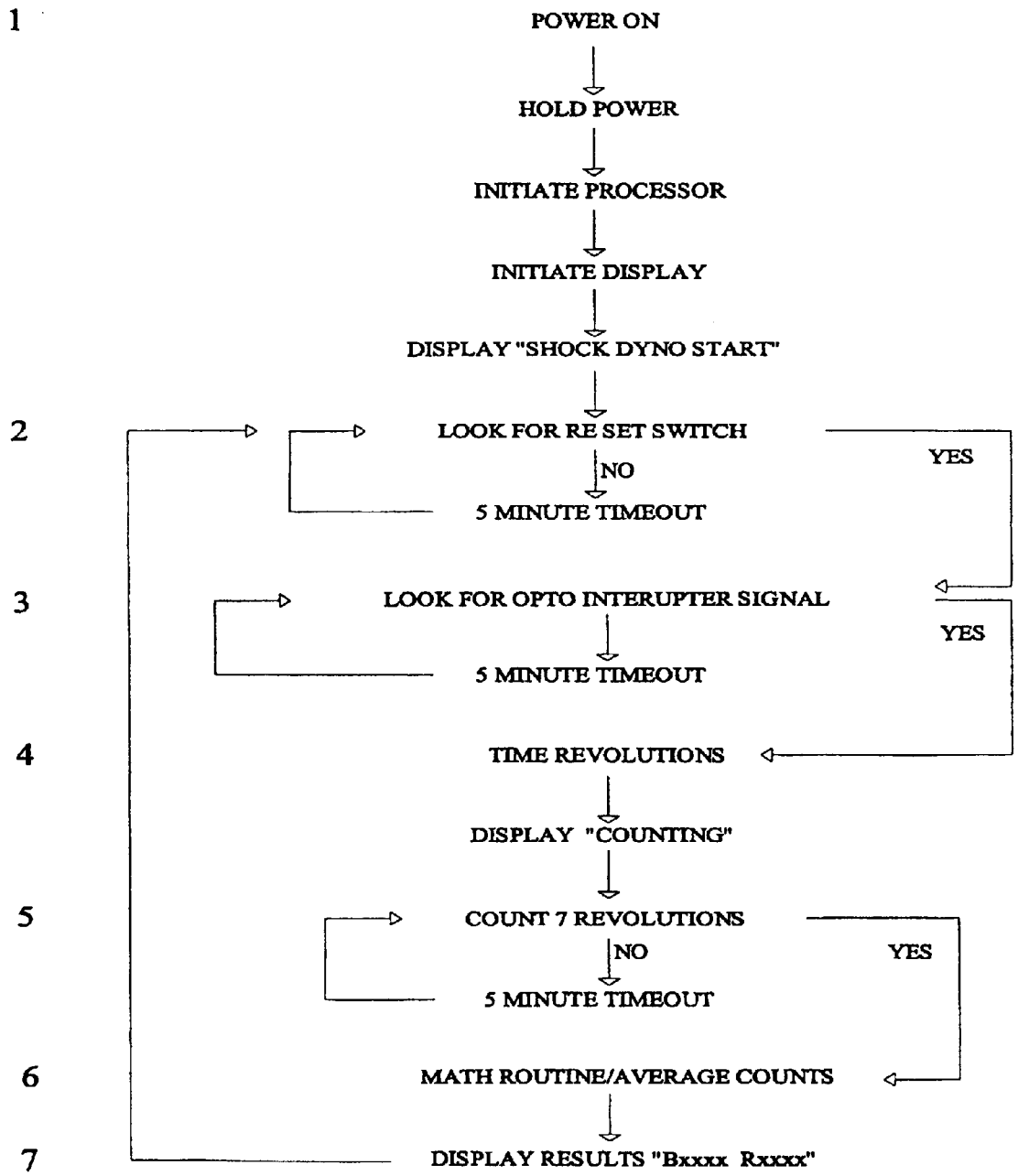
FIG. 3 is a flow chart of the steps taken by the timing and display controller.

The steps taken by the timing and data display controller 8 are illustrated by the flow chart shown in FIG. 3. As shown in the flow chart, a momentary switch, prior to releasing the weight, powers up the timing and data display controller 8. The momentary switch initializes the microprocessor and also initializes the display, (for example, to show "SHOCK DYNO START"). The timing and data display controller 8 then waits for activation of a second momentary switch which resets the timing and data display controller 8 (step 2). The timing and data display controller 8 then displays, for example, "BUMP 0000 REBOUND 0000".

The operator then releases the weight on the drive system; this begins the actuation of the shock 1 and the rotation of the trigger through the optical interrupter switch 10. The microprocessor then detects the signal from the optical interrupter switch (step 3). Once the microprocessor detects the signal it begins timing the revolutions in milliseconds (step 4). While the revolutions are being timed (based on the changing signal output of the optical interrupter switch 10) the timing and data display controller 8 displays, for example, "COUNTING".

As previously mentioned, the timing and data display controller 8 times, for example, seven revolutions. The microprocessor 16 (shown in FIG. 3 and discussed below) then studies the seven optical interrupter switch open circuit times and deletes the fastest and slowest times. It also studies the seven optical interrupter switch closed circuit times and deletes the fastest and slowest times. The microprocessor 16 then averages the remaining five switch open circuit times and averages the remaining five switch closed circuit times (step 6).

Next, the timing and data display controller 8 displays the average as "BUMP XXXX REBOUND XXXX" which denotes the average time in milliseconds (XXXX) for one compression (BUMP) stroke and one extension (REBOUND) stroke of the tested shock (step 7). In one embodiment, each of these steps is timed out (i.e., the timing and data display controller 8 powers off) in five minutes if the microprocessor 16 receives no signal from the reset switch or optical interrupter switch 10.

Figure 4:
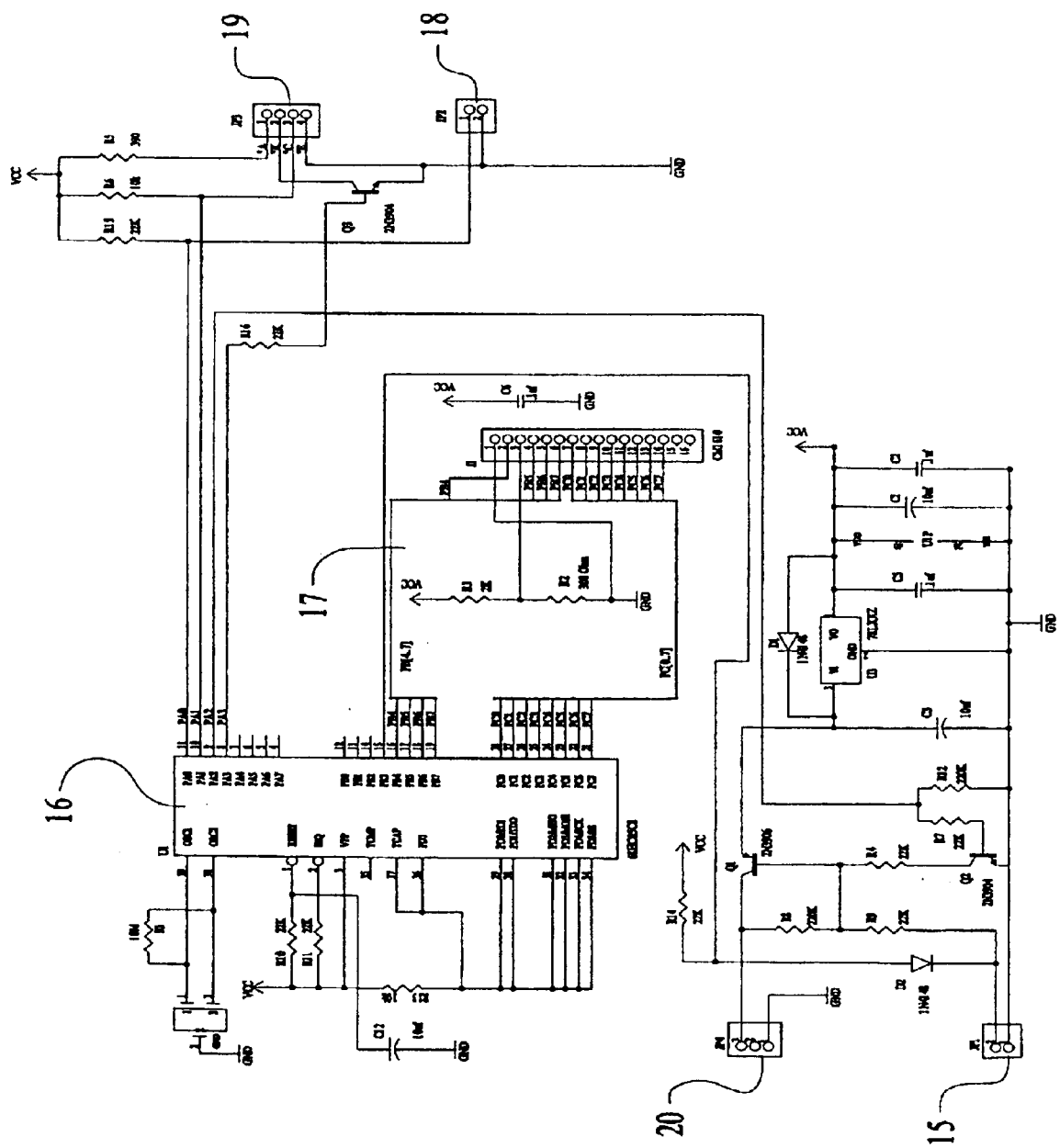
FIG. 4 is a circuit diagram of the timing and display controller.

A circuit diagram of the electronic components that may be used to implement the steps outlined in FIG. 3 is shown in FIG. 4. Referring to FIG. 4, the timing and data display controller 8 is powered up or initialized by a momentary switch connected to the momentary switch input 15. The microprocessor 16 contains the firmware that implements the steps described above. The liquid crystal display, 17, provides the information of status and data to the operator. A reset momentary switch connected to the reset momentary switch connector 18 zeros the display and alerts the microprocessor to look for the optical interrupter switch signal present on the optical interrupter switch input 19. A power supply (e.g., a 9V DC battery 20) supplies power to a voltage regulation circuit, as shown.

Figure 5:
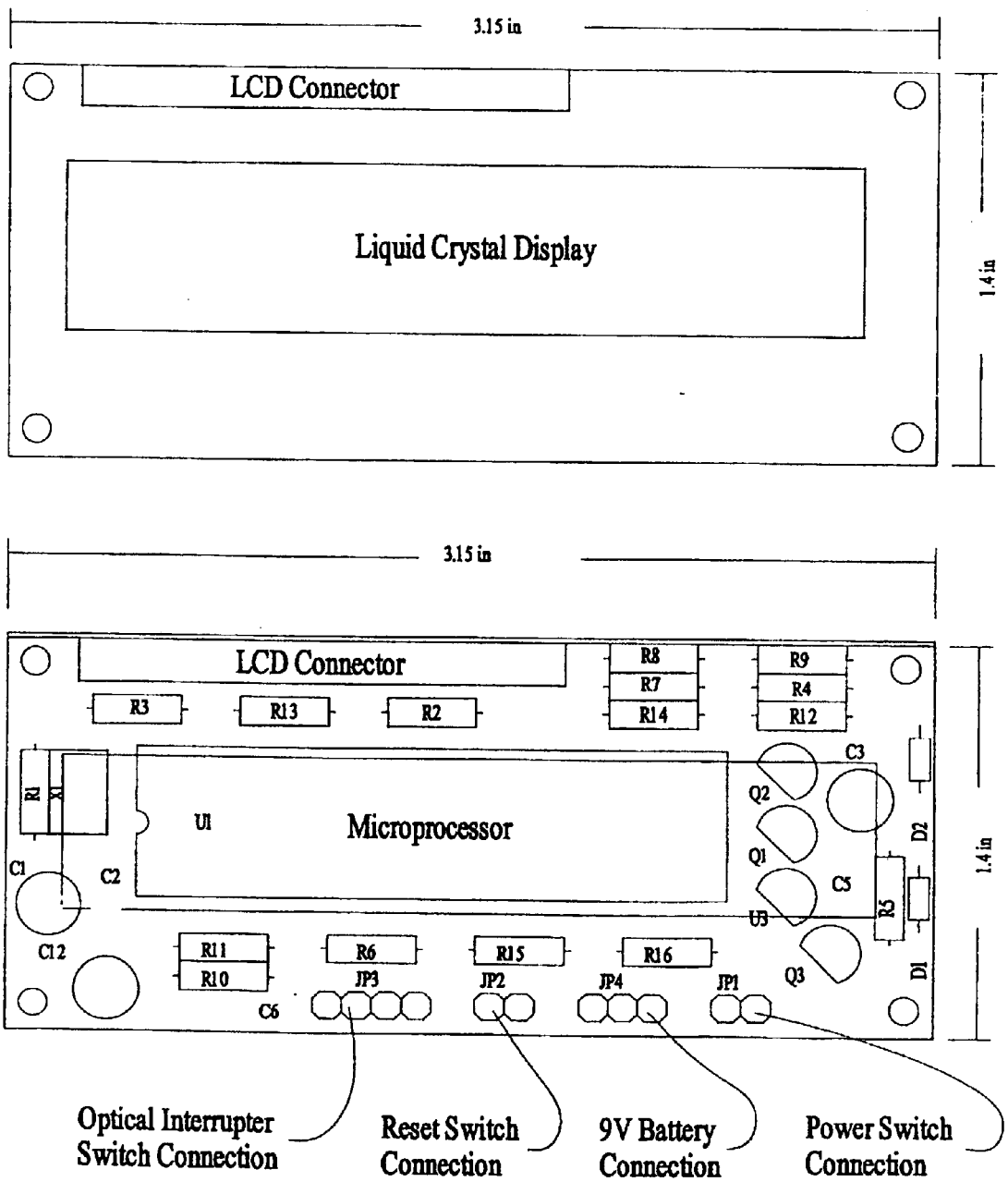
FIG. 5 is a diagram of the timing and display controller that shows an exemplary layout of the electronic components in the circuit diagram.

FIG. 5 shows one exemplary circuit board layout of the electronic components detailed in FIG. 4.

As discussed above, according to the present invention, it is possible to test shock absorbers, specifically those on small and scale vehicles, with a convenient, reliable, compact and relatively economical dynamometer 100.

The foregoing description of an implementation of the invention has been presented for purposes of illustration and description. It is not exhaustive and does not limit the invention to the precise form disclosed. Modifications and variations are possible in light of the above explanation or may be acquired from practicing of the invention.

What is claimed is:

1. A shock dynamometer for testing a shock absorber, the shock dynamometer comprising:
   a lower mounting for securing an end of the shock absorber;
   a drive crank coupled to the lower mounting for actuating the shock absorber;

a drive weight coupled to the drive crank for actuating the drive crank;

a trigger plate coupled to the drive crank; and a sensor responsive to rotation of the trigger plate.

2. The shock dynamometer of claim 1, wherein the trigger plate is a semi-circular plate, and wherein the sensor is an optical interrupter switch.

3. The shock dynamometer of claim 1, wherein the lower mounting is a rotator mount.

4. The shock dynamometer of claim 1, wherein the lower mounting comprises an ANSI mounting threaded section and a UNC mounting threaded section.

5. The shock dynamometer of claim 1, further comprising an upper mounting for securing an opposite end of the shock absorber.

6. The shock dynamometer of claim 5, further comprising a slotted vertical support member, and wherein the upper mounting is coupled to the slotted vertical support member.

7. The shock dynamometer of claim 5, wherein the upper mounting comprises an ANSI mounting threaded section and a UNC mounting threaded section.

8. A shock dynamometer for testing a shock absorber, the shock dynamometer comprising:

a shock absorber drive crank;

a drive weight coupled to the drive crank for actuating the drive crank;

a sensor responsive to actuation of the drive crank; and a timing controller coupled to the sensor for analyzing sensor output.

9. The shock dynamometer of claim 8, wherein the timing controller comprises a microprocessor and firmware executed by the microprocessor.

10. The shock dynamometer of claim 8, further comprising a display coupled to the microprocessor.

11. The shock dynamometer of claim 8, wherein the sensor is an optical sensor.

12. The shock dynamometer of claim 8, wherein the timing controller determines a compression stroke time.

13. The shock dynamometer of claim 8, wherein the timing controller determines an extension stroke time.

14. The shock dynamometer of claim 8, wherein the timing controller determines a plurality of extension stroke times and an extension stroke time average.

15. The shock dynamometer of claim 8, wherein the timing controller determines a plurality of compression stroke times and a compression stroke time average.

16. A shock dynamometer comprising:

a drive crank;

a drive cable spool coupled to the drive crank;

a drive weight coupled to the drive cable spool;

a sensor responsive to actuation of the drive crank; and a timing controller coupled to the sensor for analyzing sensor output.

17. The shock dynamometer of claim 16, further comprising a vertically slotted tower and an upper shock mounting coupled to the vertically slotted tower.

18. The shock dynometer of claim 16, wherein the sensor is an optical sensor.

19. The shock dynometer of claim 16, further comprising an upper shock mounting comprising an ANSI mounting threaded section and a UNC mounting threaded section.

20. The shock dynometer of claim 16, further comprising a lower shock mounting comprising an ANSI mounting threaded section and a UNC mounting threaded section.

* * * * *